United States Patent
Ina et al.

(10) Patent No.: US 6,521,889 B1
(45) Date of Patent: Feb. 18, 2003

(54) DUST PARTICLE INSPECTION APPARATUS, AND DEVICE MANUFACTURING METHOD USING THE SAME

(75) Inventors: Hideki Ina, Yokohama (JP); Kenji Itoga, Tokyo (JP)

(73) Assignees: Canon Kabushiki Kaisha, Tokyo (JP); Mitsubishi Denki Kabushiki Kaisha, Tokyo (JP)

(*) Notice: Subject to any disclaimer, the term of this patent is extended or adjusted under 35 U.S.C. 154(b) by 124 days.

(21) Appl. No.: 09/689,860

(22) Filed: Oct. 13, 2000

(30) Foreign Application Priority Data

Oct. 15, 1999 (JP) .......................... 11-293568

(51) Int. Cl.$^7$ .............................................. G01N 21/89
(52) U.S. Cl. ................ 250/306; 356/237.3; 356/237.4; 356/237.5; 356/335; 356/336
(58) Field of Search ...................... 250/306; 356/237.4, 356/237.3, 237.5, 335, 336

(56) References Cited

U.S. PATENT DOCUMENTS 5,270,794 A * 12/1993 Tsuji et al. ................. 356/371
5,623,340 A * 4/1997 Yamamoto et al. ......... 356/237
5,936,726 A * 8/1999 Takeda et al. ........... 356/237.2

OTHER PUBLICATIONS

Japan. "Automatic Inspection of Foreign Particles on Patterned Sample by Means of Polarized Laser", by Akiyama et al., Journal of Measurement Automatic Control Association, vol. 17, No. 2, pp237–242, 1981.*

* cited by examiner

*Primary Examiner*—Bruce Anderson
*Assistant Examiner*—Zia R. Hashmi
(74) *Attorney, Agent, or Firm*—Fitzpatrick, Cella, Harper & Scinto

(57) ABSTRACT

A dust particle inspection apparatus for detecting size information and height information of a dust particle on the surface of a mask or a wafer, as well as a device manufacturing method using the same, are disclosed. Light from a light source is directed to a predetermined surface to be inspected, and reflection light from a dust particle on the predetermined surface is detected by a detecting system. An output signal of the detecting system is processed by a signal processing system, so that size information of the dust particle along the predetermined surface and height information thereof with respect to a direction of a normal to the predetermined surface are detected.

15 Claims, 10 Drawing Sheets

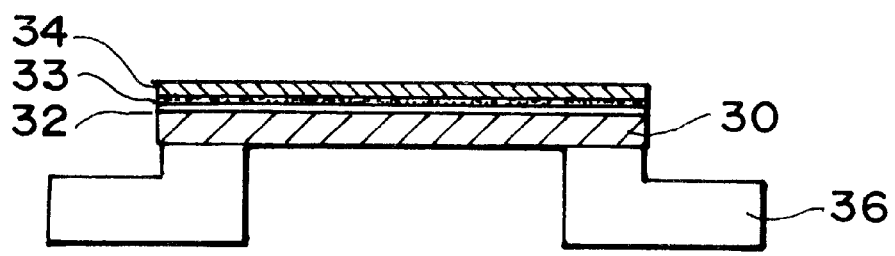
F I G. 13
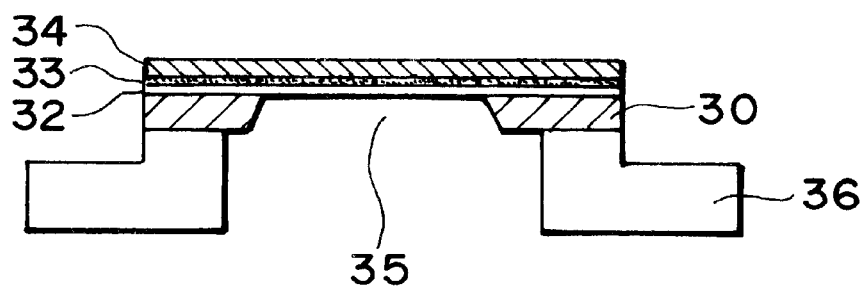
F I G. 14
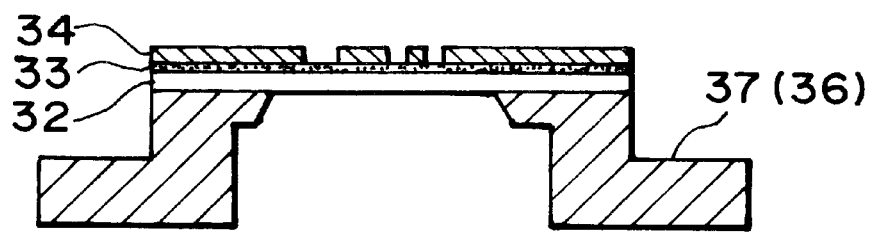
F I G. 15

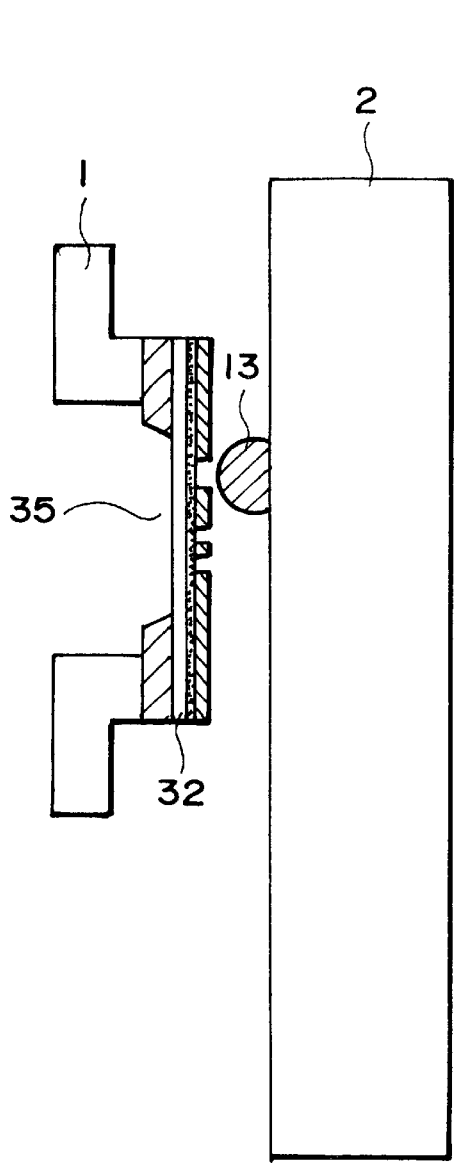 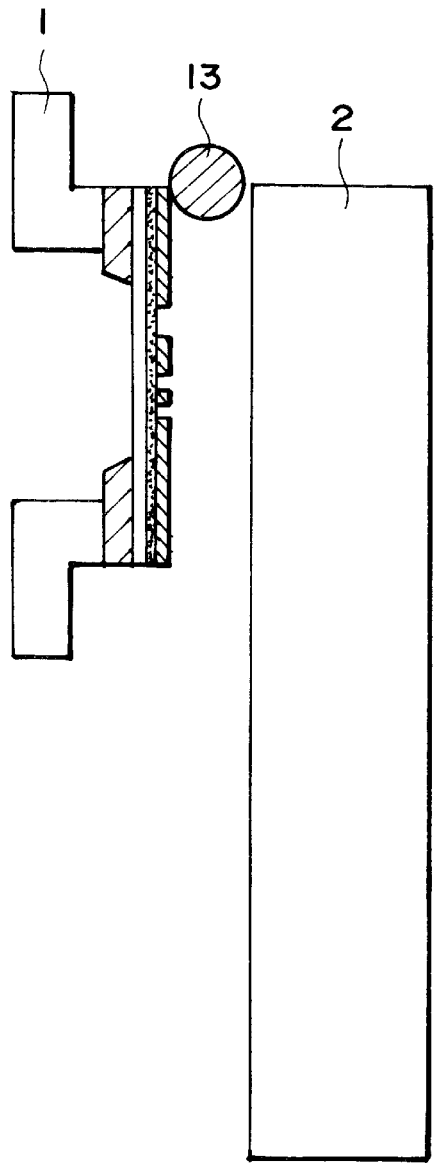
F I G. 18    F I G. 19

DUST PARTICLE INSPECTION APPARATUS, AND DEVICE MANUFACTURING METHOD USING THE SAME

FIELD OF THE INVENTION AND RELATED ART

This invention relates to a dust particle inspection apparatus and a device manufacturing method using the same. The present invention is suitably usable for inspection of the state of presence/absence a foreign substance such as a dust particle (presence/absence of or the size of such particle) or the height of such dust particle (magnitude in a direction of a normal to a surface where the particle is adhered to), upon a substrate such as a mask, for example, having a circuit pattern formed thereon, particularly in the field of the manufacture of devices such as semiconductor devices (e.g., IC or LSI), CCDS, liquid crystal panels or magnetic heads, for example. Thus, the present invention is suitably applicable to the manufacture of high-precision devices such as described above.

Particularly, the present invention provides specific advantageous effects when the same is applied to a semiconductor exposure method called a "Proximity X-ray Lithography" (hereinafter, "PXL") wherein an X-ray beam of a wavelength 7–10 angstroms emitted from an electron accumulation ring (synchrotron radiation unit) is used as a light source and wherein a pattern of a mask is transferred to a wafer at a unit magnification while the mask and the wafer are dispose d opposed to each other with a gap of a few tens microns maintained therebetween.

Generally, in IC manufacturing processes, a circuit pattern formed on a substrate such as a mask is transferred to a wafer, being coated with a resist, by use of an exposure apparatus. If in this procedure there is a foreign substance such as a dust particle upon the surface of the substrate, such particle is also transferred in the transfer process to decrease the yield of the IC or LSI production.

In the conventional PXL procedure, a mask is disposed opposed to a wafer with a gap (clearance) of 10–30 microns kept therebetween, and the mask pattern is transferred to the wafer through Fresnel diffraction.

As regards exposure apparatuses of PXL type, an exposure apparatus having a largest exposure range of 52 mm square has currently been proposed. The largest exposure range of 52 mm square means that, even in the unit-magnification exposure, for a wafer of a size of 4 inches or larger, the whole surface of the wafer can not be exposed through a single exposure operation.

In the PXL exposure process, the whole surface of a wafer is exposed while the wafer is moved sequentially as in a repetition reduction exposure apparatus, called a "stepper". Thus, in this respect, an exposure apparatus of PXL type may be called as a "unit magnification X-ray stepper".

As regards the resolution, a result of 100 nm or less, or a result of 20 nm or less based on the alignment result, has been reported. Also, it is recognized that the PXL has a potential for an exposure process for devices of 1 gigabit or more. One special feature of the PXL is an X-ray mask.

Conventional X-ray mask manufacturing processes will now be explained, with reference to FIG. 5 and the like. Here, as regards the thicknesses of a mask, a wafer and a film thereon, for better understanding, they are illustrated in proportions different from practical proportions.

In the manufacture of a PXL mask, as shown in FIG. 5, a silicon (Si) wafer 30 is prepared as a substrate. Then, as shown in FIG. 6, a SiC film 31 of a thickness of 2–3 microns, called a membrane, is formed on the Si wafer 30.

When the SiC film 31 is produced on the Si wafer 30, practically the film is formed on the top and bottom faces of the substrate as well as the side face thereof. Since, however, the bottom face and the side face do not provide a function, in FIG. 6 and later, the films formed there are not illustrated.

Subsequently, as shown in FIG. 7, the surface of the SiC film 31 is flattened by polishing, whereby a SiC film 32 is provided. Then, as shown in FIG. 8, an ITO film or $SiO_2$ film 33 is produced as an etching stopper and also for better affinity with an X-ray absorptive layer. Thereafter, as shown in FIG. 9, a material having a relatively high X-ray absorptivity such as W, Ta or $Ta_4B$, for example, is applied with a thickness 0.3–0.5 micron, as an X-ray absorptive material 34. Then, as shown in FIG. 10, through various processes such as resist application, desired patterning with an electron beam patterning apparatus, development, etching, and resist separation, a pattern is defined by the X-ray absorbing material 34.

Subsequently, as shown in FIG. 11, a portion of the Si wafer 30 at a side thereof remote from the pattern is removed by back etching, such that X-rays can transmit through the Si wafer portion 35 corresponding to the exposure range. Finally, as shown in FIG. 12, the peripheral portion of the Si wafer 30 is mounted on a frame 36, by which an X-ray mask is accomplished.

It is well known that, in order to minimize the patterning error, an additional procedure may be performed after the step of FIG. 10, so that, as shown FIG. 13, the Si wafer 30 is mounted on a frame 36 and then, as shown in FIG. 14, the portion of the Si wafer 30 corresponding to the exposure range is back etched to enable transmission of X-rays therethrough. Thereafter, as shown in FIG. 15 and like FIG. 12, various processes such as resist application, desired patterning with an electron beam patterning apparatus, development, etching, and resist separation may be performed so that a pattern is defined by the X-ray absorbing material 34.

However, if the patterning process is performed after the frame 36 is mounted to the Si wafer 30, there may arise a problem that the Si wafer 30 and the frame 36 are detached from each other due to heat. In consideration of it, in many cases, the X-ray mask is produced by taking processes such as shown in FIGS. 5–12.

As regards the frame, it may be called as a "support ring". As for the material thereof, Pyrex or SiC is used. For mounting it to the membrane, an anodic bonding process or an adhesive agent is used.

A proposal has been made to use an integral type frame 37 (FIG. 15) wherein the frame 36 of FIG. 13 is made of the same material as the Si wafer 30, that is, to make the Si wafer substrate 30 and the frame 36 as a unit.

There is a problem peculiar to the PXL. That is, when a dust particle of a size larger than the exposure gap between a mask and a wafer is sandwiched between the mask (particularly, a SiC membrane) and the wafer, the SiC portion of the mask may be destroyed.

Seemingly, if the exposure gap is 10 microns, there is no possibility that a dust particle larger than 10 microns is present between a wafer and a mask. This is particularly so because a good yield rate is regarded absolutely important in the semiconductor manufacture. However, this is not correct. Particularly, if a dust particle is attached to a peripheral portion outside the effective area of a wafer or mask, a problem peculiar to the PXL arises.

As regards such dust particle adhered to the peripheral portion of a mask or wafer, it has not raised a critical problem since the current semiconductor manufacturing procedure uses, in most cases, an exposure apparatus called "optical exposure apparatus" wherein a pattern of a mask is projected and printed on a wafer through a projection optical system. In such optical exposure apparatus, there is a distance of 1 cm or more between the wafer and the projection optical system of the exposure apparatus. Further, the peripheral portion of a wafer is not used for the IC production. Therefore, as regards a dust particle at the wafer peripheral portion, no inspection process is currently performed.

However, according to the observation of the wafer peripheral portion made by the inventors of the subject application, in many cases there were large dust particles at the wafer peripheral portion. It has been found that, even in the semiconductor manufacture wherein a good yield rate is regarded absolutely important, in many cases there are large dust particles at the wafer peripheral portion.

As long as optical exposure apparatuses are used, no critical problem may arise from a dust particle at the wafer peripheral portion. However, the problem is just not yet known. To be exact, there is a possibility that such dust particle is displaced (separated) from the wafer peripheral portion, for some reason, to a wafer pattern portion (effective area) to cause a critical problem. A wafer inspection apparatus for inspecting any dust particle on a wafer having a pattern already formed thereon, may be used to perform the inspection, to prevent a decrease of the yield.

However, in the PXL procedure, the presence of a dust particle at the peripheral portion can cause a serious problem.

It is now assumed that, as shown in FIG. 16, a dust particle 13 is adhered to a peripheral portion of a wafer 2, and that a PXL exposure process is performed with a predetermined gap kept between the wafer and a mask 1. When the wafer 2 is thereafter moved such as shown in FIG. 17 for exposure of a region near the peripheral portion of the wafer 2, a force is applied to the dust particle 13 attached to the wafer 2.

At this time, since the dust particle 13 contacts to a portion of the Si material 30 of the mask 1, not having been back etched, this does not cause breakage of the mask 1.

However, if after the exposure the wafer 2 moves for exposure of another region thereof, since a force has been applied to the dust particle 13, the motion of the wafer 2 causes separation of the dust particle 13 from the wafer 2. Thus, the dust particle 13 also moves to another place.

As the dust particle 13 moves, it may be attached to a region corresponding to the SiC portion 32 of the pattern 35 of the mask, having been back etched, as shown in FIG. 18. In that occasion, when the exposure and wafer motion process is repeated, a force is applied again to the dust particle 13. Since the SiC portion 32 there has a thickness of 2–3 microns, the SiC portion may be destroyed.

Although what described above concerns an example wherein a dust particle is adhered to a peripheral portion of the wafer 2, the same applies to a case where a dust particle is attached to a peripheral portion of the mask 1.

FIG. 19 illustrates it. That is, a dust particle 13 is attached to a mask 1 at a first shot of wafer exposure. A force is applied to the dust particle 13 as the same is sandwiched between the mask and the wafer 2. The mask 1 is not broken thereby because of a similar reason as the case where a dust particle is attached to the peripheral portion of the wafer, as described hereinbefore. As the wafer 2 moves thereafter, the dust particle 13 may be moved and adhered to a region corresponding to the SiC portion 32 where the Si material portion of the mask 1 has been back etched. In that occasion, the mask 1 may be destroyed, similarly.

As described above, a dust particle at a peripheral portion of a mask or wafer, which does not cause serious inconveniences in the optical exposure method, particularly when it is larger than the exposure gap, may cause a critical problem of breakage of a mask.

Further, even if the mask is not broken, if a dust particle being moved displaces onto a wafer and it is not detected by inspection for some other reason, the semiconductor device may not function well. Thus, it may cause a decreased yield rate. This is similar to the problem in the optical exposure method.

The inventors of the subject application have made investigations about dust particle inspection to the whole surface of a wafer and an X-ray mask, including the peripheral portion thereof, by use of a wafer dust particle inspection apparatus for detecting a dust particle on a wafer having a pattern already formed thereon.

As regards the wafer dust particle inspection apparatuses for detecting a dust particle on a wafer having a pattern already formed thereon, there is a type which is based on such detection principle that a polarized light is obliquely projected on a wafer so that, by a circuit pattern, the light is reflected while keeping its polarization characteristic, whereas, by a dust particle, the light is reflected with a non-polarized state.

Inspection apparatuses using this detection principle have already been developed as product machines, and they practically assure a high throughput that the detection time of only 1 minute or shorter is necessary for an 8-inch wafer, as well as a high reliability. They have contributed to higher yield rates.

However, as described above, in optical exposure apparatuses, no concern has been put on the peripheral portion of a wafer.

According to the investigations made by the inventors of the subject application, it has been found that, by using such wafer dust particle inspection apparatus, for both a mask and a wafer, a dust particle can be detected while being distinguished from an etched portion of the Si material at the periphery. However, it has also been found that, in the vicinity of the periphery of the mask, there is a possibility that a signal larger than one for a usual dust particle may be produced to cause an erroneous detection as the presence of a large dust particle.

The cause of such erroneous detection will be such as follows. As regards a mask, currently, no specific design has been made to the structure of the peripheral portion. Therefore, in a CVD apparatus, a dust particle may be adhered to a peripheral portion of a wafer when the same is supported. Also, there may be non-uniformness of SiC film thickness or of absorptive material film thickness, due to influences applied from the peripheral portion of the mask. Further, there may be a peeled film portion produced as the film is scratched by tweezers or the like during the mask handling, for example, when the mask is mounted on a frame.

If these particles or surface irregularities are measured by using a current dust particle inspection apparatus for a wafer having a pattern formed thereon, it may be discriminated that there is a large dust particle, being larger than 10 microns.

In current wafer dust particle inspection apparatuses, the size of a dust particle is discriminated on the basis of a correlation table for a particle and a corresponding signal output detected beforehand. In this detection principle, the dust particle is taken as providing isotropic light scattering. On the other hand, from the peeled film portion or from the film thickness irregularities, because of its complicated structure, the light may be refracted and scattered and, thus, it may be detected. In that occasion, a large output signal as compared with a signal output of isotropic scattering light from a dust particle, is detected consequently. Thus, as regards the peeled film or the like, it may be detected as being a large dust particle, being larger than its real size, such as more than 10 microns.

Further, it has been found that, in the peripheral portion of a wafer, a dust particle may be crushed during the conveyance or as the wafer is mounted on a carrier, such that a dust particle of a large size, although it has no height, may be detected.

However, such peeled film, film non-uniformness, or a flat dust particle on the wafer is not a particle which has a height of 10 microns or more. Thus, it has no potential of causing breakage of the mask.

SUMMARY OF THE INVENTION

It is accordingly an object of the present invention to provide a dust particle inspection apparatus and a device manufacturing method using the same, by which a dust particle having a potential of causing breakage of a mask and a dust particle not having such potential can be discriminated and inspected, to thereby facilitate the manufacture of large integration devices.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 5–14 are schematic views, respectively, for explaining processes for producing an X-ray mask in accordance with the present invention.

FIG. 15 is a schematic view of a X-ray mask according to the present invention, wherein a mask and a frame are made into an integral structure.

FIGS. 16–18 are schematic views, respectively, for explaining how a mask is broken as a dust particle adhered to a peripheral portion of a wafer moves when the mask and the wafer are disposed opposed with a predetermined exposure gap.

FIGS. 19 and 20 are schematic views, respectively, for explaining how a mask is broken as a dust particle adhered to a peripheral portion of the mask moves when the mask and the wafer are disposed opposed with a predetermined exposure gap.

DESCRIPTION OF THE PREFERRED EMBODIMENTS

Figure 1:
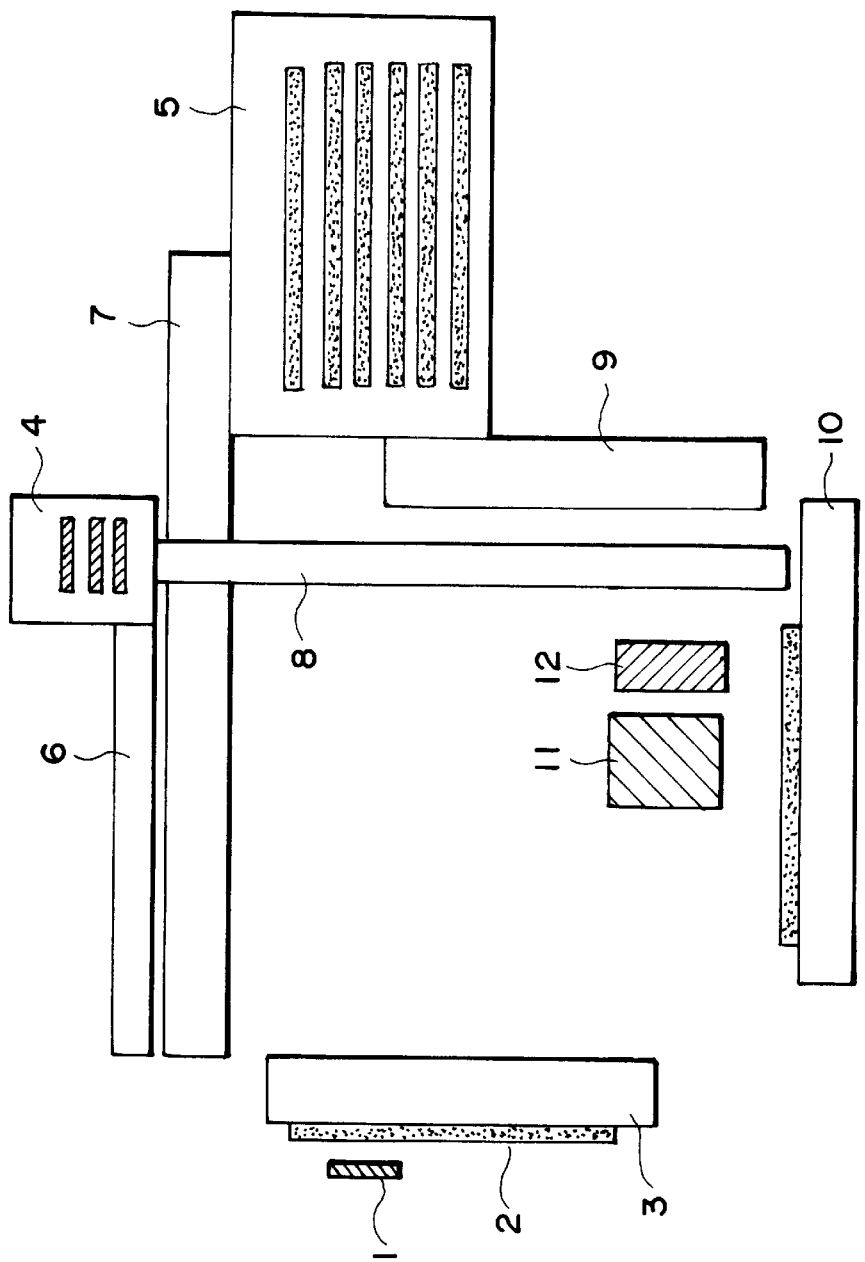
FIG. 1 is a schematic view of a main portion of a dust particle inspection apparatus according to a first embodiment of the present invention.

FIG. 1 is a schematic view of a main portion of a dust particle inspection apparatus (mask inspection apparatus) according to the present invention, and it shows components inside a PXL exposure apparatus.

In this embodiment, as regards a foreign substance such as a dust particle adhered to a subject to be inspected, such as a mask or wafer, size information related to the size of the particle along the surface to be inspected, as well as height information related to the height or size of the particle in a direction of a normal to the surface to be inspected, are detected.

A mask and a wafer disposed opposed to each other with a small gap (exposure gap) kept therebetween. When a pattern of the mask is going to be transferred to the wafer by exposure, the presence of a dust particle of a size larger than the exposure gap, between the mask and the wafer, should be prevented as much as possible.

Particularly, in this embodiment, in an exposure method wherein an exposure process is performed while a mask and a wafer are disposed with a predetermined gap kept therebetween, the inspection is carried out through a detection system (first detecting means) for projecting light to the mask and the wafer and for discriminating the size of a dust particle on the basis of the magnitude of a signal output of reflection light therefrom, and another detection system (second detecting means) for directly detecting a height of the dust particle. The inspection may be done inside the exposure apparatus or a coater developer.

In FIG. 1, a wafer 1 and a mask 2 are placed in an exposure apparatus vertically, so that an X-ray beam of a wavelength 7–10 angstroms emitted horizontally from an electron accumulation ring (SR) of a synchrotron radiation unit can be efficiently projected on the wafer 1. If the wafer 1 and the mask 2 are placed horizontally, the X-ray beam has to be deflected by 90 deg. by using a mirror, but efficient right-angle reflection is not easy to accomplish.

The exposure of the mask 1 and the wafer 2 disposed vertically is carried out while an exposure gap of 10–30 microns is kept therebetween. A largest exposure range is 52 mm square. As regards a 300 mm wafer, for example, exposures of 40 shots or more are carried out while moving a vertical type X-Y stage 3, carrying the wafer 1 thereon and having an interferometer.

Prior to setting, vertically, a mask 2 and a wafer 2 at the exposure position, plural masks and plural wafers are kept in clean environment boxes 4 and 5, called a mask SMIF and a wafer FOUP, respectively. As required, each mask and each wafer are taken out from the boxes and conveyed by means of a mask conveying system 6 and a wafer conveying system 7, respectively.

As shown in FIG. 1, there are another mask conveying system 8 and another wafer conveying system 9 for conveying a mask 2 and a wafer 1, respectively, for performing dust particle inspection to the mask 2 surface and the wafer 1 surface. The function of these conveying systems 8 and 9 may be provided by the above described conveying systems 6 and 7, respectively.

By using the conveying system 8 or 9, a mask 2 or a wafer 1 is placed on an X-Y stage 10 for dust particle inspection.

This stage 10 differs from the vertical type X-Y stage for wafer exposure. It comprises a horizontal type stage, and it does not need a very high precision. The mask 2 or the wafer 1 is placed on the X-Y stage 10 with its surface, to be opposed to the wafer or the mask, kept facing up, and then presence/absence of a dust particle adhered to the surface thereof as well as the height of the particle are detected by means of dust particle inspection machines 11 and 12.

The inspection machine 11 is based on an inspection method using oblique incidence and polarization, and it comprises a detecting system for discriminating the size of a dust particle on the basis of the magnitude of a signal output. By using such inspection machine 11, presence/absence of a dust particle on the whole surface of a mask or a wafer is inspected.

Details of the dust particle inspection machine according to this embodiment will now be described.

Figure 21:
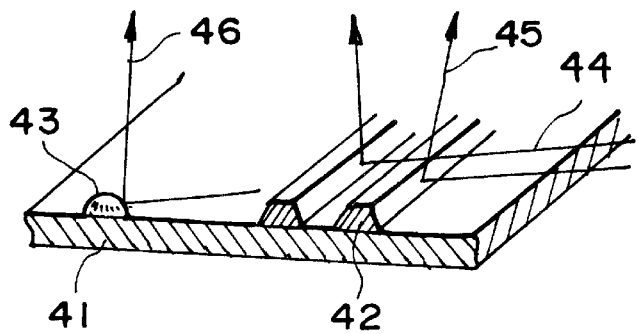
FIGS. 21–23 are schematic views, respectively, for explaining a dust particle inspection apparatus according to the present invention.

Referring to FIG. 21, if illumination light 44 is just projected onto the surface of a wafer 41 at an oblique angle ø, scattered light 43 and scattered light 44 are simultaneously produced from a pattern 42 and a dust particle 43. Therefore, the pattern 42 and the dust particle 43 can not be distinguished from each other. In consideration of it, polarized laser light is used as the illumination light 44 to enable detection of only the dust particle 43.

Figure 22:
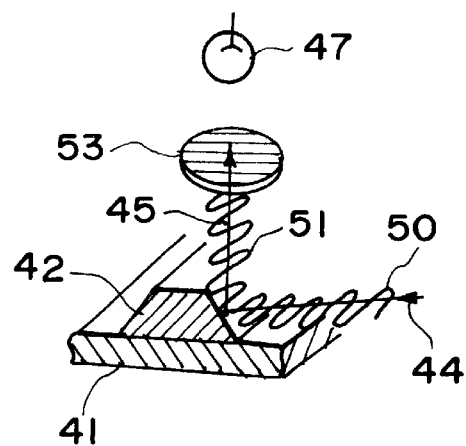

More specifically, as shown in FIG. 22, S-polarized laser light 44 is projected on a pattern 42 formed on a wafer 41. Here, where the electric vector 50 of the laser light 44 is parallel to the wafer surface, it is called as S-polarized laser illumination. Generally, when observed microscopically, the surface irregularities of the pattern 42 are sufficiently small as compared with the wavelength of the illumination light, and thus the surface can be regarded as being smooth, optically. Therefore, in reflection light 45 produced from the surface, the S-polarization component 51 can be well maintained.

Therefore, once an analyzer 53 for S-polarization interception is inserted into the light path of the reflection light 45, the reflection light 45 can be blocked and it does not reach a photoelectric converting element 47.

Figure 23:
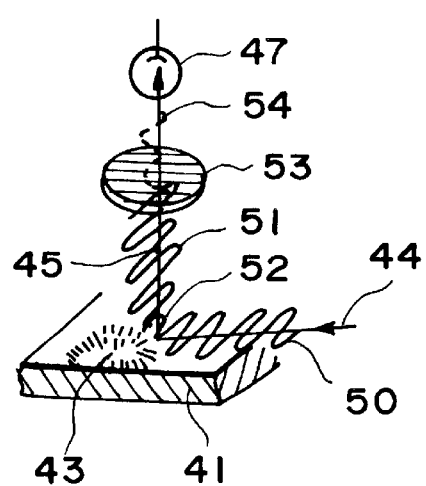

On the other hand, as shown in FIG. 23, the scattered light 46 from the dust particle 43 contains a P-polarized component 52 in addition to the S-polarized component. This is because the surface of the particle 43 is very rough so that the polarization is dissolved thereby and, as a result, the P-polarized component 52 is produced. Thus, by detecting the P-polarized component 52 passed through the analyzer 53 by using the photoelectric converting element 47, detection of the dust particle 43 is enabled.

Here, as regards reflection light from the pattern 42, where the longitudinal direction of the pattern 42 has a right angle with respect to the laser light 44, the reflection light 45 is completely blocked by the analyzer 53. If the angle differs from the right angle, the light is not completely blocked. Details of this are discussed in "Journal of Measurement Automatic Control Association", Vol. 17, No. 2, pp 237–242, 1981. According to this paper, only the reflection light from the pattern which is in a range of ±30 deg. from the right angle can enter an objective lens disposed above the wafer. Therefore, the reflection light 45 from the pattern inside this range is not completely blocked by the analyzer 53. Since, however, the intensity of such light is sufficiently small as can be distinguished from the scattered light from a dust particle of 2–3 micron, practically there is no problem.

As regards the dust particle inspecting machine 12, it functions to directly measure the height (length in a direction of a normal to the surface being inspected) of such dust particle that the inspection machine 11 has discriminated it as being at the peripheral portion of the mask 2 or the wafer 1 and having a size (length) corresponding to the exposure gap so that it has a potential of destroying the mask 2 when the mask 2 and the wafer 1 are disposed opposed with the exposure gap kept therebetween. The process of measuring the height will be described later with reference to FIG. 2.

Only a mask or a wafer having been inspected by using the inspection machines 11 and 12 and discriminated as having no dust particle, is conveyed to the exposure position by means of the mask conveying system 6 or the wafer conveying system 7. At the exposure position, the mask or the wafer are rotated by 90 degrees by the conveying system, and it is disposed vertically. Thereafter, the exposure process is carried out.

Figure 2:
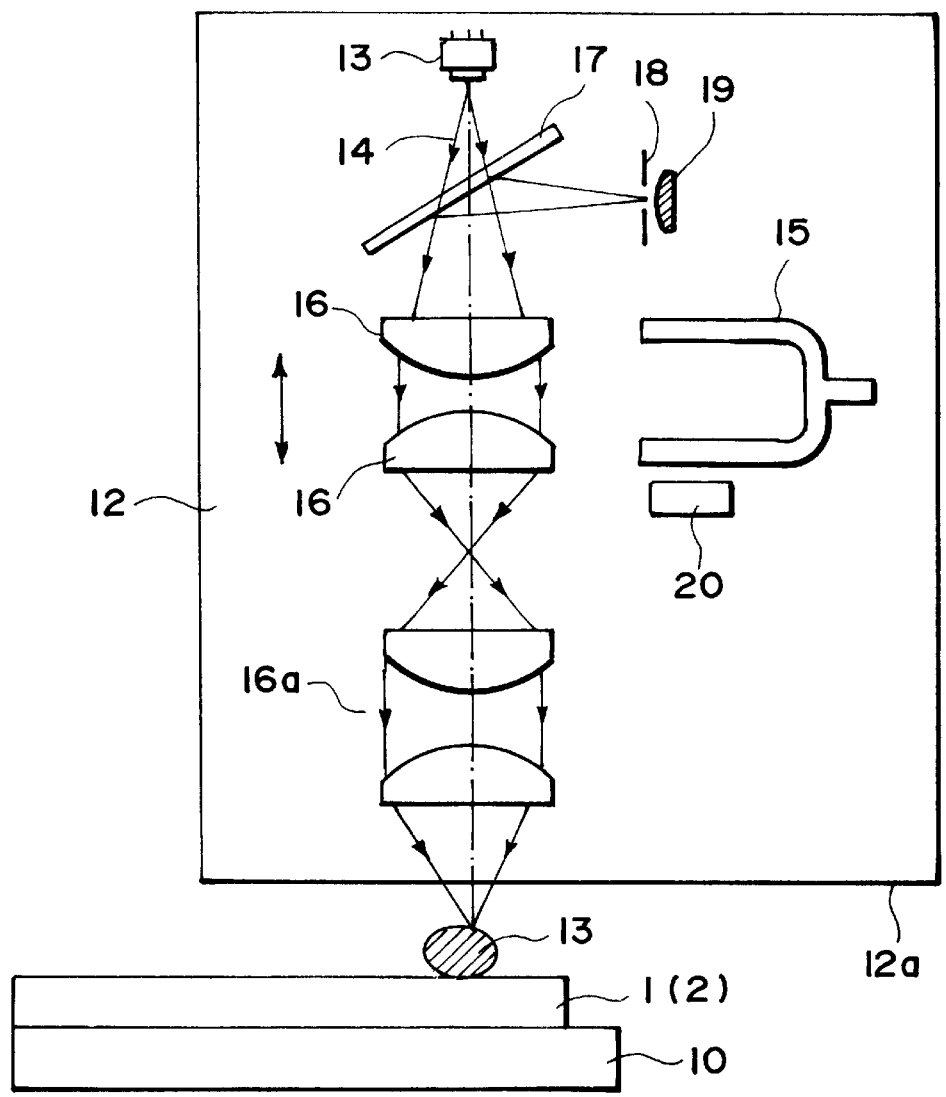
FIG. 2 is a schematic view of a main portion of second detecting means in an embodiment of the present invention.

FIG. 2 is a schematic view of a main portion of the inspection machine 12 of FIG. 1. The inspection machine 12 directly measures the height of only a dust particle discriminated by the other inspection machine 11 of FIG. 1 as having a potential of damaging the mask.

The inspection machine 12 shown in FIG. 2 comprises a confocal detection system using laser as a light source, and it can measure the thickness (height) of a transparent or non-transparent member precisely and stably. The machine shown in FIG. 2 may be one which is commercially available as "Long-Range Laser Focus Displacement Gauge LT-8100", manufactured by Kabushiki Kaisha Kiensu, Japan. The principle of particle height detection will be described below.

In FIG. 2, laser light 14 emitted from a laser 13 which can be regarded as a point light source, goes through a half mirror 17 and through an objective lens 16 which is vertically oscillated at a high speed by means of a tuning fork 15. Then, it passes through a lens system 16a and is focused (collected) on a subject to be inspected (i.e., a dust particle 13 in FIG. 2). The light reflected by the subject 13 goes back along its oncoming path, and it is reflected by the half mirror 17. Then, the light passes through a pinhole 18 and reaches a light receiving element 19. In accordance with the confocal principle, when the laser light is focused on the subject 13, the reflection light therefrom forms a minimum spot light of a size in terms of the diffraction limit, at the position of the pinhole 18, and it impinges on the light receiving element 19. The position of the tuning fork 15 at that moment is measure by means of a sensor 20, by which the distance to the subject 13 from a reference plane (reference plane 12a of the machine 12) can be detected.

Subsequently, a wafer or a mask is taken as a subject, and a dust particle inspecting X-Y stage 10 is moved to perform measurement of the height of the wafer surface or the mask surface from the reference plane 12a of the inspection machine. By this, the height of the dust particle 13 can be detected.

The dust particle inspecting X-Y stage 10 serves to move only the region about a large dust particle as being discriminated by the other inspection machine 11, on the basis of the position taken for the inspection by the inspection machine 11 and the size information of the dust particle, such that the height of the dust particle is detected by the dust particle inspection machine 12 which comprises a detection system capable of detecting the height.

As regards the measurement time, the other inspection machine 11 can operate at a higher speed, and it needs not longer than 1 minute for the whole surface of an 8-inch wafer.

Since in most cases a dust particle to be considered is adhered to the peripheral portion of a mask or a wafer, as regards the inspection time of the inspection machine 12, even if it is not very fast, the total exposure throughput may not be slowed down thereby.

As described hereinbefore, the dust particle inspection apparatus of this embodiment is equipped with a dust particle inspection machine 11 for discriminating the size of a dust particle (magnitude along the surface direction of the surface being inspected) on the basis of the magnitude of a signal output, and another dust particle inspection machine 12 capable of detecting the height thereof. On the basis of the information provided by the inspection machine 11 which discriminates the size of a dust particle in accordance with the magnitude of a signal output the inspection machine 12 detects the height of the dust particle. This enables exact detection of a large dust particle having a potential of damaging the mask. Further, the inspection does not decrease the throughput largely.

Particularly, in the conventional dust particle inspection machines for a wafer having a pattern, the size is discriminated on the basis of a signal, detected and in accordance with a correlation table for a particle and a corresponding signal output detected beforehand. Namely, the size of a dust particle is determined on the basis of the magnitude of the signal output. The measurement is done thereby. It differs from detecting the height of a dust particle having a potential of mask breakage. This leads to a possibility that a film thickness irregularity or a peeled film portion at the peripheral portion of a mask, for example, is discriminated as being a large dust particle, since it produces a large signal output as compared with a signal output to be caused by isotropic scattering from a dust particle.

As compared therewith, in this embodiment of the present invention, in relation to the peripheral portion of a mask (since in most cases a large dust particle is present at the peripheral portion), a detection system similar to such conventional dust particle inspection apparatus is employed to discriminate the size of the dust particle on the basis of the magnitude of a signal output. If, as a result of the detection thereby, the presence of a large dust particle is detected, then the height of such dust particle is directly measured by using another detection system having a function for detecting the height thereof. On the basis of it, whether the dust particle is harmful (causing mask breakage) or not is discriminated. With this procedure, the erroneous detection such as described hereinbefore can be avoided.

In summary, in this embodiment, since detection of the size only on the basis of a signal output is insufficient, the height of a dust particle in question is directly measured. On the basis of it, the particle is removed and thus the manufacture of large integration devices is facilitated.

In the first embodiment of FIG. 1, a dust particle inspection machine 11 comprising a detection system for discriminating the size of a particle on the basis of the magnitude of a signal output as well as a dust particle inspection machine 12 capable of detecting the height, are disposed inside an exposure apparatus. However, the present invention is not limited to it.

For example, for both of a mask and a wafer, inspection machines each comprising a stand-along type detection system may be provided outside an exposure apparatus. Substantially the same advantageous results are attainable, provided that the cleanness after the inspection is kept.

Rather than the stand-alone type, an in-line structure being connected to an exposure apparatus through, a computer or the like, may be used. In such structure, a wafer dust particle inspection apparatus may be provided inside a coater developer which performs resist application and development. In that occasion, the cleanness of a mask and a wafer after the inspection should be maintained, like the case of the stand-alone type structure. The dust particle inspection in the coater developer may be done either before or after the resist application.

The place where a dust particle is generated is important. Unless the place is not found, the inspection may be done both before and after the resist application, for example.

Further, it is not always necessary to dispose the two detection systems in one and the same apparatus. For a dust particle having a potential of decreasing the yield rate, detailed inspection may be done by use of a stand-alone type dust particle inspection machine 11 comprising a detection system for discriminating the size of the particle on the basis of the magnitude of a signal output. On the other hand, a dust particle inspection machine 12 capable, of detecting the height may be disposed inside a coater developer or an exposure apparatus, for example, to perform the height detection only for the peripheral portion of a mask or a wafer.

If the place where dust particles are generated is found, the best efficiency is obtainable by carrying out the inspection just after it. If, however, the location is not found and where the inspection should be made by using a single dust particle inspection machine, rather than using plural dust particle inspection machines, the inspection may be done while placing a mask and a wafer at the exposure position. In that occasion, it is not necessary to keep the cleanness after the inspection, as required in the case where a stand-alone type inspection machine is used.

However, in such case, the exposure process and the inspection process can not be done simultaneously and, therefore, the throughput decreases. Of course, plural wafers may be placed on the X-Y stage 3 (FIG. 1) having an interferometer, and the exposure and the inspection may be done simultaneously. However, the X-Y stage 3 having an interferometer requires a higher precision for the global alignment. Enlargement in size is not harmonious with it. Also, it causes an increase of the cost.

In the embodiment of FIG. 2, the dust particle inspection machine 12 has been described with reference to a confocal system. However, the present invention is not limited to this. Provided that the height can be detected, any detection principle may be used to accomplish the present invention.

Figure 3:
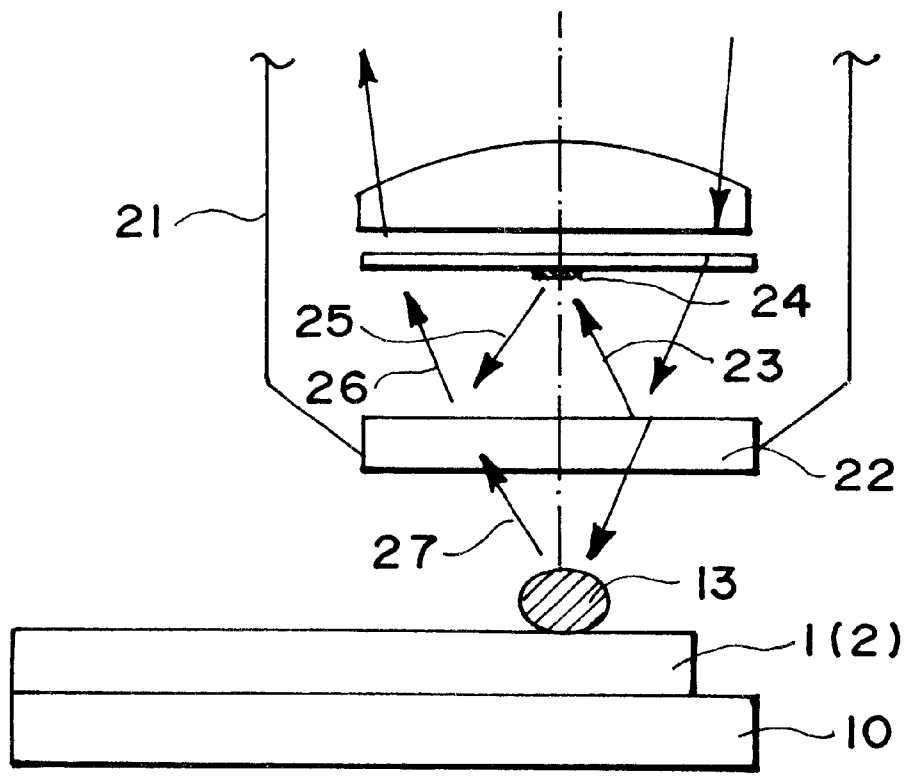
FIG. 3 is a schematic view of a Mirau interferometer system in an embodiment of the present invention.
Figure 4:
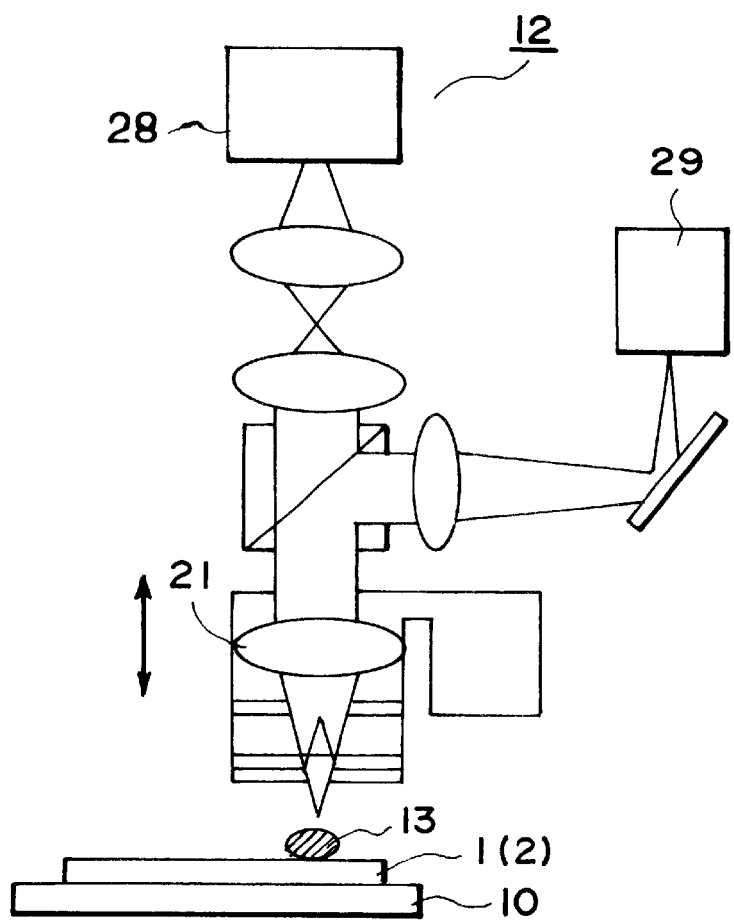
FIG. 4 is a schematic view of another example of a Mirau interferometer system in an embodiment of the present invention.
Figure 5:
Figure 6:
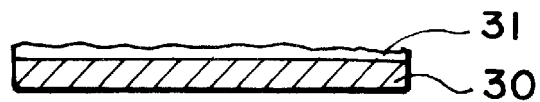
Figure 7:
Figure 8:
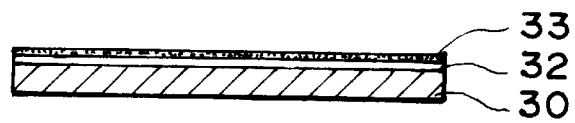
Figure 9:
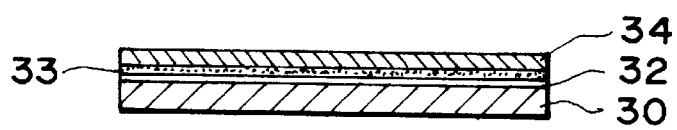
Figure 10:
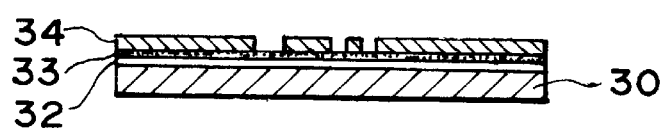
Figure 11:
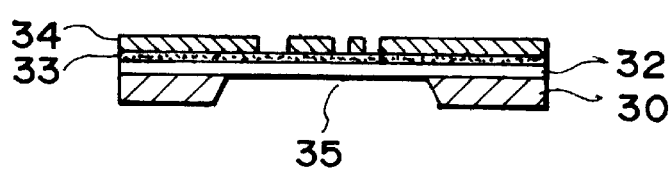
Figure 12:
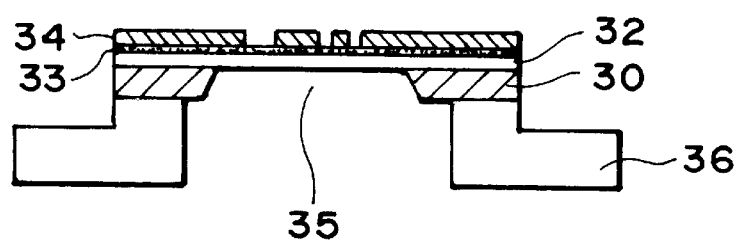
Figure 16:
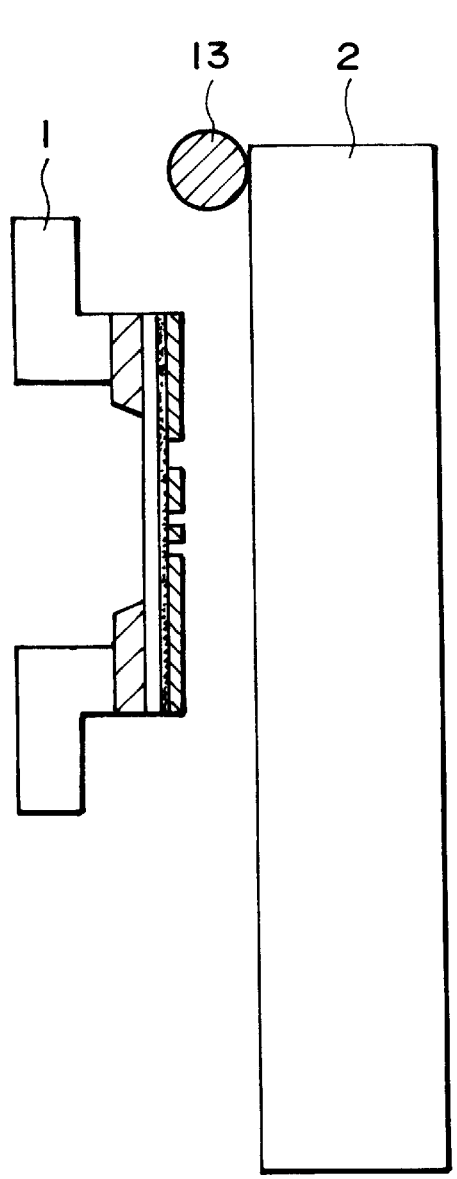
Figure 17:
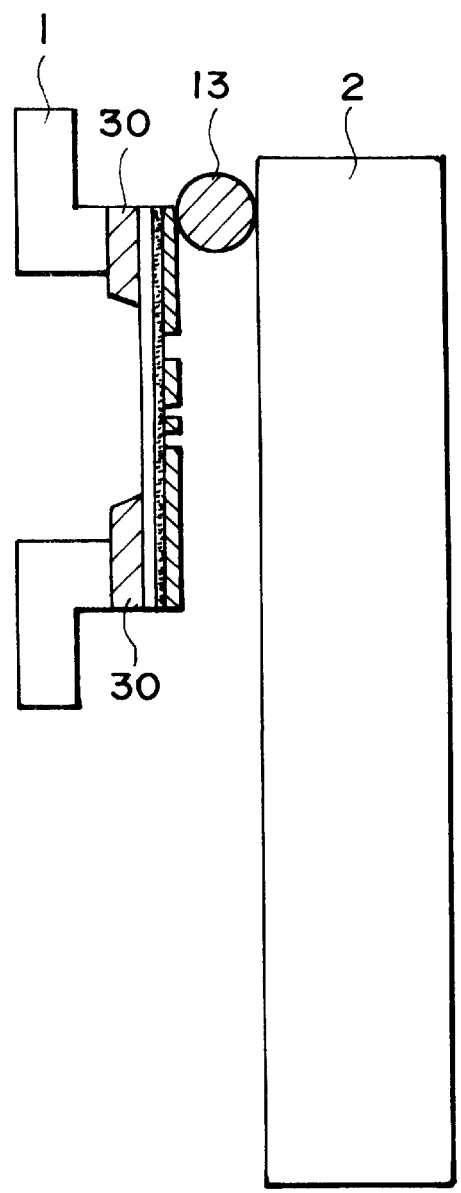
Figure 20:
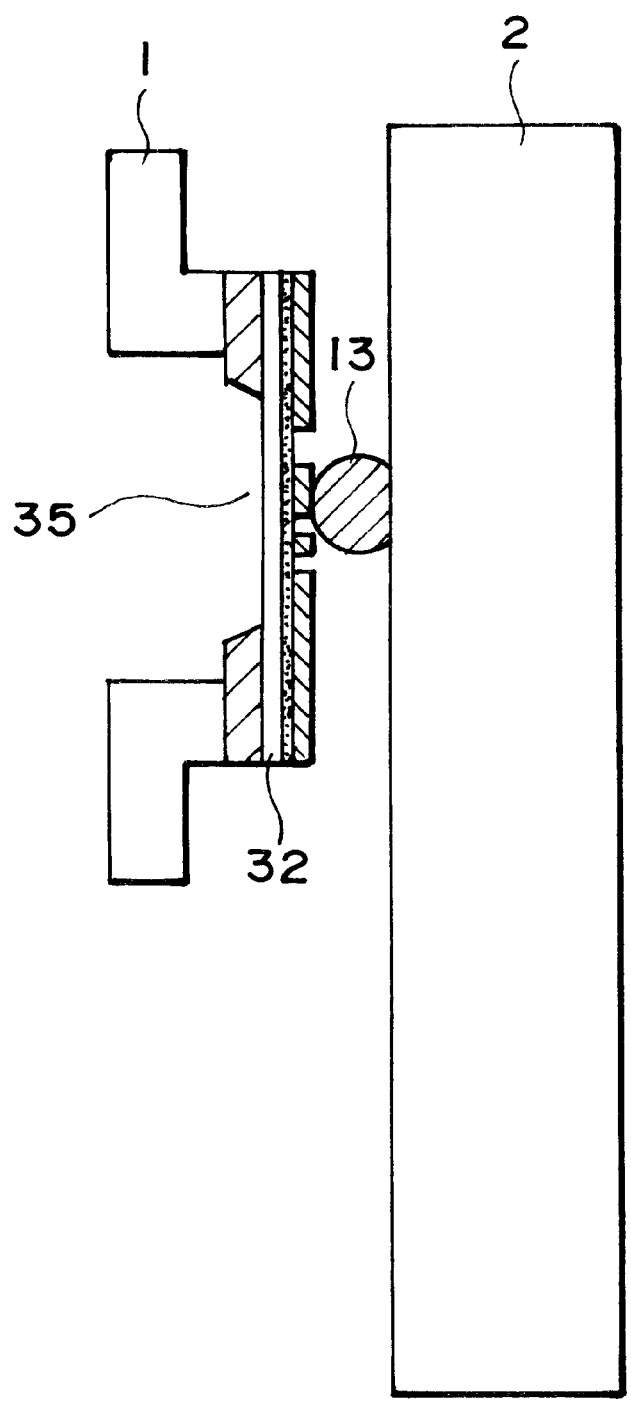

FIGS. 3 and 4 are schematic views of a main portion of a dust particle inspection machine which can be incorporated into a dust particle inspection apparatus of the present invention and which can perform the height detection.

An embodiment of a dust particle inspection machine capable of detecting the height, will be described with reference to FIGS. 3 and 4. The system illustrated is called also as a Mirau interferometer system or a white interferometer system, and products are available from Zygo Co. FIG. 3 illustrates the principle of Mirau interferometer. FIG. 4 shows the general structure of the optical system in the inspection apparatus.

In FIG. 3, description will be made only with respect to those light rays impinging from the right-hand side. Practically, there are light rays impinging from the left-hand side, but they are omitted for simplicity. In FIG. 3, a half mirror 22 is disposed between an objective lens 21 and a subject (dust particle 13 in this drawing). A reflecting member 24 is disposed only at the portion where the light 23 reflected by the half mirror 22 is focused. The light 25 as reflected by the reflecting member 24 is then reflected by the half mirror 22. By taking the thus reflected light 26 as reference light, it is caused to interfere with reflection light 27 from the subject 13. The system described above is an interference system called a Mirau interferometer. Practically, as regards the light rays coming from the left-hand side, an interferometer is similarly defined by reference light and reflection light from the subject 13.

Since, however, the structure described above provides only interference information along a flat plane, product machines available from Zygo Co. are arranged so that the objective lens 21 as a whole shown in FIG. 4 are moved in an optical axis direction by means of a piezoelectric device (not shown) and that interference information corresponding to each piezoelectric device position is photoelectrically converted by an image pickup device 29 such as a CCD camera, for example. Through subsequent various processings, three-dimensional shape information is produced. By using white light from al halogen lamp, for example, as a light source 28, an interferometer having a small coherence length is provided, and a high resolution is attained thereby. In this respect, this system is called also as a white interferometer system.

By using this Mirau interferometer as a dust particle inspection machine 12 having a function of height detection, a dust particle inspection apparatus of the present invention can be accomplished, like the case using a confocal system as has been described with reference to FIG. 1.

In FIGS. 1, 2 and 3, description has been made with reference to an optical height detecting system. However, the present invention is not limited to it. For example, an atomic force microscope (AFM) or a probe type profiler may be used to detect the height of a dust particle. When they are used, there occurs contact with the subject to be inspected (even in the tapping mode which is most widely used as the measuring mode in current AFM systems). Therefore, they can be used only in cases where there is no possibility of damaging the subject of inspection.

As regards inspection of a dust particle adhered to a mask, when a dust particle having a certain reproducibility is detected by two inspection machines (for example, a case where there are plural irregularities at a peripheral portion of a SiC film, and a detection system for discriminating the size of a particle on the basis of a signal output detects presence of a large dust particle, whereas a height detection system discriminates it as can be disregarded), if the result is reproduced by plural measurements, a dust particle map peculiar to that mask may be prepared. This eliminates the necessity of performing the inspection every time by using the height detection dust inspection machine. The increase of throughput attainable with it depends on the state of adhesion of dust particles on the mask. This can be called, in a wide sense, as a mask offset which may be incorporated into a computer for controlling the exposure machine. By controlling the dust particle map while assigning IDs to masks, a higher-throughput inspection operation can be accomplished.

For production of devices in accordance with the present invention, a mask and/or a wafer is conveyed out of a container unit and, by use of a dust particle inspection apparatus, size information and height information of a dust particle on the mask surface or the wafer surface is inspected. If absence of a harmful dust particle on the mask or wafer surface is discriminated by the inspection apparatus, then the mask or the wafer is loaded at the exposure position of the exposure apparatus. If presence of a harmful dust particle is discriminated, the mask or the wafer is washed by a cleaning unit and, thereafter, it is inspected again by the inspection apparatus. After removal of the harmful dust particle is discriminated, the mask or the wafer is loaded at the exposure position. Then, the pattern of the mask is transferred, by exposure, to the wafer. Thereafter, the thus exposed wafer is treated by a development process and the like, whereby devices are produced.

As described above, the present invention accomplishes a dust particle inspection apparatus by which a dust particle having a potential of destroying a mask and a dust particle having no such potential can be distinguished and detected separately. Also, the present invention provides a device manufacturing method and an exposure method using the same.

In accordance with the present invention, the inspection of a dust particle adhered to an X-ray mask is carried out by using two detection systems, one of which comprises a detection system capable of measuring the height information. With this structure, a harmful dust particle and a non-harmful dust particle can be distinguished and detected separately. As a result, the inconveniences peculiar to the PXL, that is, breakage of a mask by a dust particle caught between the mask and a wafer and being larger than the exposure gap, can be avoided without an erroneous detection.

While the invention has been described with reference to the structures disclosed herein, it is not confined to the details set forth and this application is intended to cover such modifications or changes as may come within the purposes of the improvements or the scope of the following claims.

What is claimed is:

1. An inspection apparatus for inspecting a predetermined surface to be inspected, comprising:

light source means;

directing means for directing light from said light source to the predetermined surface;

detecting means for detecting reflection light from a dust particle on the predetermined surface; and signal processing means for processing an output signal of said detecting means to detect size information of the dust particle along the predetermined surface and height information of the dust particle with respect to a direction of a normal to the predetermined surface.

2. An apparatus according to claim 1, wherein said detecting means includes first detecting means for detecting size information of the dust particle along the predetermined surface, and second detecting means for detecting height information of the dust particle with respect to a direction of a normal to the predetermined surface.

3. An apparatus according to claim 2, wherein, when a dust particle on the predetermined surface and having a preset size is detected by said first detecting means, said second detecting means detects height information of the dust particle.

4. A dust particle inspection method for detecting size information and height information of a dust particle on a predetermined surface to be inspected, by use of an inspection apparatus which comprises (i) light source means, (ii) directing means for directing light from the light source to the predetermined surface, (iii) detecting means for detecting reflection light from a dust particle on the predetermined surface, and (iv) signal processing means for processing an output signal of the detecting means to detect size information of the dust particle along the predetermined surface and height information of the dust particle with respect to a direction of a normal to the predetermined surface.

5. An exposure apparatus, comprising:

exposure means for transferring, by exposure, a pattern of a mask onto a wafer while the mask and the wafer are disposed with a predetermined gap maintained therebetween;

light source means;

directing means for directing light from said light source to at least one of the mask and the wafer;

detecting means for detecting reflection light from a dust particle on the mask or the wafer; and signal processing means for processing an output signal of said detecting means to detect size information of the dust particle along a surface of the mask or the wafer, and height information of the dust particle with respect to a direction of a normal to the mask surface or the wafer surface.

6. An apparatus according to claim 5, wherein said detecting means detects the size information and the height information of the dust particle outside an effective region of the mask surface or the wafer surface.

7. An apparatus according to claim 5 or 6, wherein said detecting means includes first detecting means for detecting size information of the dust particle and second detecting means for detecting height information of the dust particle.

8. An apparatus according to claim 7, wherein, when a dust particle on the mask surface or the wafer surface and having a preset size is detected by said first detecting means, said second detecting means detects height information of the dust particle.

9. An apparatus according to claim 5, wherein the detection of the size information and the height information of the dust particle on the wafer surface is carried out before and after application of a resist material to the wafer surface.

10. An apparatus according to claim 5, wherein, in a coater developer for applying a resist material onto the wafer surface, the detection of the size information and the height information of the dust particle on the wafer surface is carried out before and after application of the resist material to the wafer surface.

11. An apparatus according to claim 5, wherein the mask is an X-ray exposure mask.

12. A device manufacturing method, comprising the steps of:

preparing an inspection apparatus including (i) light source means, (ii) directing means for directing light from the light source to a predetermined surface to be inspected, (iii) detecting means for detecting reflection light from a dust particle on the predetermined surface, and (iv) signal processing means for processing an output signal of the detecting means to detect size information of the dust particle along the predetermined surface, and height information of the dust particle with respect to a direction of a normal to the predetermined surface;

loading at least one of a mask and a wafer accommodated in a container, into the inspection apparatus;

performing inspection of size information and height information of a dust particle on the surface of the mask or the wafer by use of the inspection apparatus;

loading the mask or the wafer at an exposure position in an exposure apparatus when absence of a harmful dust particle on the mask surface or the wafer surface is discriminated by the inspection apparatus;

repeating the inspection after the mask surface or the wafer surface is cleaned by using a cleaning apparatus, where presence of a harmful dust particle is discriminated by the inspection apparatus;

loading the mask or the wafer at the exposure position in the exposure apparatus, when, after the cleaning, removal of the harmful dust particle is discriminated;

transferring, by exposure, a pattern of the mask onto the wafer; and developing the exposed wafer, for production of a device.

13. A device manufacturing method for producing a device on the basis of an inspection method for detecting size information and height information of a dust particle on a predetermined surface, to be inspected by use of an inspection apparatus which comprises (i) light source means, (ii) directing means for directing light from the light source to the predetermined surface, (iii) detecting means for detecting reflection light from a dust particle on the predetermined surface, and (iv) signal processing means for processing an output signal of the detecting means to detect size information of the dust particle along the predetermined surface, and height information of the dust particle with respect to a direction of a normal to the predetermined surface.

14. A device manufacturing method for producing a device by use of an exposure apparatus which comprises (i) exposure means for transferring, by exposure, a pattern of a mask onto a wafer while the mask and the wafer are disposed with a predetermined gap maintained therebetween, (ii) light source means, (iii) directing means for directing light from the light source to at least one of the mask and the wafer, (iv) detecting means for detecting reflection light from a dust particle on the mask or the wafer, and (v) signal processing means for processing an output signal of the detecting means to detect size information of the dust particle along a surface of the mask or the wafer, and height information of the dust particle with respect to a direction of a normal to the mask surface or the wafer surface.

15. An exposure method, comprising the steps of:

transferring, by exposure, a pattern of a mask onto a wafer while the mask and the wafer are disposed with a predetermined gap kept therebetween;

directing light to at least one of the mask and the wafer; and detecting reflection light from a dust particle on a surface of the mask or the wafer, to detect size information of the dust particle along the mask surface or the wafer surface, and height information of the dust particle in a direction of a normal to the mask surface or the wafer surface.

* * * * *

UNITED STATES PATENT AND TRADEMARK OFFICE
CERTIFICATE OF CORRECTION

PATENT NO. : 6,521,889 B1
DATED : February 18, 2003
INVENTOR(S) : Ina et al.

It is certified that error appears in the above-identified patent and that said Letters Patent is hereby corrected as shown below:

Column 2,
Line 30, "shown" should read -- shown in --.

Column 8,
Line 46, "measure" should read -- measured --.

Column 9,
Line 15, "output" should read -- output, --;
Line 22, "signal," should read -- signal --; and
Line 67, "through," should read -- through --.

Column 10,
Line 19, "capable," should read -- capable --.

Column 11,
Line 20, "al" should read -- a --.

Signed and Sealed this

Second Day of December, 2003

JAMES E. ROGAN
*Director of the United States Patent and Trademark Office*